United States Patent [19]

Hege et al.

[11] Patent Number: 4,730,042
[45] Date of Patent: Mar. 8, 1988

[54] COMPOUNDS 1 OR 3-HYDROXY-4-BENZYL-6-METHYL-7-(4-ISOPROPYLAMINO-BUTOXY)-1,3-DIHYDRO[3,4-C]PYRIDINE AND 2-METHYL-3-(4-ISOPROPYL-AMINOBUTOXY)-4-(1'-MORPHILINOMETHYL)-5-HYDROXYMETHYL-6-BENZYL PYRIDINE, USEFUL FOR TREATING CARDIAC ARRHYTHMIAS

[75] Inventors: Hans-Guenther Hege, Neustadt; Gerhard Eisen, Schifferstadt; Horst Koenig, Ludwigshafen; Gerda von Philipsborn, Weinheim, all of Fed. Rep. of Germany

[73] Assignee: BASF Aktiengesellschaft, Ludwigshafen, Fed. Rep. of Germany

[21] Appl. No.: 868,699

[22] Filed: May 30, 1986

[30] Foreign Application Priority Data

Jun. 1, 1985 [DE] Fed. Rep. of Germany ....... 3519693

[51] Int. Cl.⁴ ................. C07D 491/048; C07D 413/12
[52] U.S. Cl. ..................... 544/124; 546/116; 546/194; 546/281; 546/300

[58] Field of Search .............. 546/116, 281, 194, 300; 544/124; 514/351, 302, 227, 318, 343

[56] References Cited

U.S. PATENT DOCUMENTS

| | | | |
|---|---|---|---|
| 4,206,117 | 6/1980 | von Philipsborn et al. | 514/255 |
| 4,374,841 | 2/1983 | Descamps et al. | 514/351 |
| 4,383,998 | 5/1983 | Esanu | 514/302 |

Primary Examiner—Alan L. Rotman
Attorney, Agent, or Firm—Keil & Weinkauf

[57] ABSTRACT

Pyridine derivatives of the formula

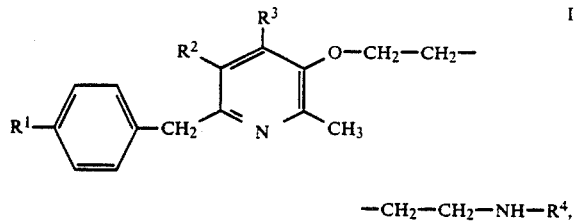

where $R^1$ to $R^4$ have the meanings stated in the description, and their preparation.

The substances are useful for treating disorders.

3 Claims, No Drawings

COMPOUNDS 1 OR 3-HYDROXY-4-BENZYL-6-METHYL-7-(4-ISO-PROPYLAMINO-BUTOXY)-1,3-DIHYDRO[3,4-C]PYRIDINE AND 2-METHYL-3-(4-ISOPROPYL-AMINOBUTOXY)-4-(1'-MORPHILINOMETHYL)-5-HYDROXYMETH-YL-6-BENZYL PYRIDINE, USEFUL FOR TREATING CARDIAC ARRHYTHMIAS

The present invention relates to novel pyridine derivatives, processes for their preparation, and their use for the treatment of disorders.

German Laid-Open Application DOS No. 2,711,655 describes pyridinyl aminoalkyl ethers which have antiarrhythmic and/or local anesthetic actions. The most well known among these compounds is barucainid (Example 34 of stated German Laid-Open Application).

We have found compounds which have a superior action.

The present invention relates to pyridine derivatives of the formula I

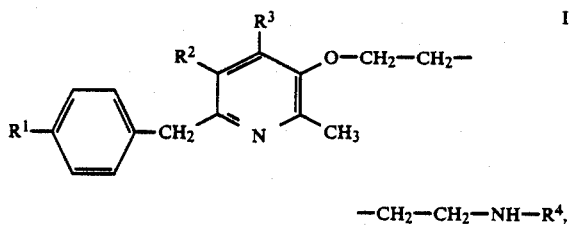

where $R^1$ is hydrogen or hydroxyl, $R^2$ is hydroxymethyl, $R^3$ is dimethylaminomethyl, pyrrolidinomethyl, piperidinomethyl, pyridinomethyl or morpholinomethyl, or $R^2$ and $R^3$ together may form the group —CH$_2$—O—CH$_2$—, where a hydrogen atom may be replaced by hydroxyl or methoxy, and $R^4$ is n-propyl, isopropyl or n-butyl, and their salts with physiologically tolerated acids.

The compounds of the formula I, where $R^1$ has the stated meanings, $R^2$ is hydroxymethyl, $R^3$ is morpholino, or $R^2$ and $R^3$ together form the —CH$_2$—O—CH$_2$—, —CHOH—O—CH$_2$— or —CH$_2$—O—CHOH— group, and $R^4$ is isopropyl, are preferred.

Physiologically tolerated acids which are particularly suitable for salt formation are hydrohalic acids, sulfuric acid, phosphoric acid, nitric acid, fumaric acid, aliphatic, alicyclic, aromatic or heterocyclic carboxylic or sulfonic acids, such as formic acid, acetic acid, propionic acid, succinic acid, glycolic acid, lactic acid, malic acid, tartaric acid, citric acid, ascorbic acid, maleic acid, pyruvic acid, benzoic acid, anthranilic acid, p-hydroxybenzoic acid or salicyclic acid, methanesulfonic acid, ethanesulfonic acid, hydroxyethanesulfonic acid, ethylenesulfonic acid, halobenzenesulfonic acids, toluenesulfonic acid, cyclohexylaminosulfonic acid or sulfanilic acid. Other acids are described in Fortschritte der Arzneimittelforschung, volume 10, pages 224–225, Brikhäuser-Verlag, Basle and Stuttgart, 1966.

The compounds of the formula I can be prepared by a process in which (a) a pyridinol of the formula II

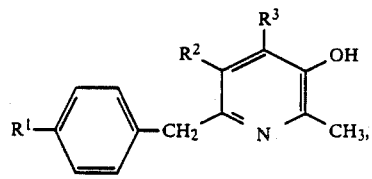

where $R^1$, $R^2$ and $R^3$ have the stated meanings, is reacted with a compound of the formula III $$X-CH_2-CH_2-CH_2-CH_2-NHR^4 \qquad III,$$

where $R^4$ has the stated meanings and X is a reactive group, or (b) a pyridinol of the formula II is reacted with a compound of the formula IV $$Y-CH_2-CH_2-CH_2-CH_2-Z \qquad IV,$$

where Y and Z are each halogen, and the product is then reacted with an anion of the formula V $$NH_2-R^4 \qquad V,$$

where $R^4$ has the stated meanings, or (c) an amine of the formula VI

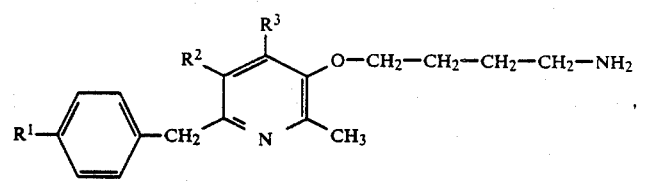

where $R^1$, $R^2$ and $R^3$ have the stated meanings, is reacted with a compound of the formula VII $$X-R^4 \qquad VII,$$

where X and $R^4$ have the stated meanings, or (d) where $R^2$ and $R^3$ together form the group —CH$_2$—O—CH$_2$— in which a hydrogen atom is replaced by a hydroxyl group, a compound of the formula VIIIa or VIIIb

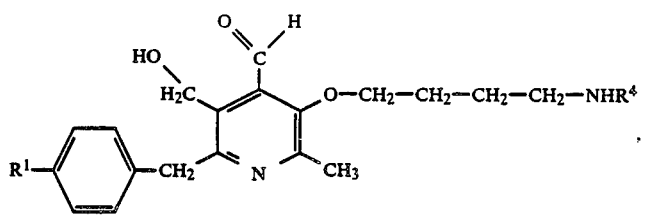

VIIIa or

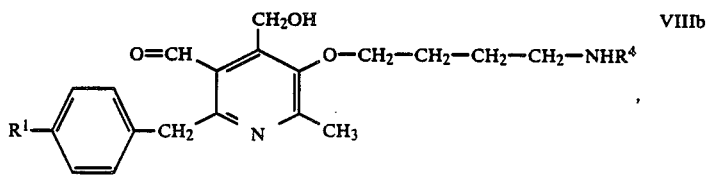

VIIIb where $R^1$ and $R^4$ have the stated meanings, is converted in the presence of an acid, and the compound thus obtained is, if desired, converted to its salts with physiologically tolerated acids.

The reaction (a) is advantageously carried out in a solvent at from 0° to 150° C., preferably from 20° to 100° C. Advantageous solvents are lower alcohols of 1 to 4 carbon atoms, in particular methanol or ethanol, lower aliphatic ketones, in particular acetone, and benzene and alkyl- and halobenzenes, such as chlorobenzene or toluene, aliphatic or cyclic ethers, such as diethyl ether, tetrahydrofuran or dioxane, dimethylformamide and dimethyl sulfoxide. If an ether is used as the solvent, hexamethylphosphorotriamide may advantageously be added as an additional solvent.

In an advantageous version, particularly where the pyridinol does not contain any readily hydrolyzable functional groups, a two-phase solvent mixture, in particular a mixture of water with a chlorohydrocarbon, such as dichloromethane, or a benzene hydrocarbon, such as benzene or toluene, is used, and the conventional method of phase-transfer catalysis, as described by, for example, M. Makosza in Pure and Applied Chemistry, 1975, No. 43, page 439, is employed. The preferred bases in this case consist of mixtures of an alkali metal hydroxide, in particular sodium hydroxide, and a quaternary ammonium base or a phosphonium base, which is used in a catalytic amount in the form of its salt, eg. triethylbenzylammonium chloride, tetrabutylammonium hydrogen sulfate or tributylhexadecylphosphonium bromide.

An example of a reactive group X is, in particular, a hydroxyl group which is esterified with a strong inorganic or organic acid, especially a hydrohalic acid, such as hydrochloric acid, hydrobromic acid or hydriodic acid, or sulfuric acid, or a strong organic sulfonic acid, eg. benzenesulfonic acid, methanesulfonic acid or 4-toluenesulfonic acid. X is preferably chlorine, bromine or iodine.

The reaction is advantageously carried out in the presence of an equivalent or excess amount of a base as an acid acceptor, for example an alkali metal hydroxide, carbonate or alcoholate, in particular the corresponding sodium or potassium compounds.

The reaction can also be carried out using the compound II in the form of its alkali metal salt, in particular the sodium or potassium salt. Salt formation is effected using one of the above alkali metal compounds or, particularly where an aprotic solvent is used, sodium amide, potassium amide, sodium hydride or potassium hydride.

The process conditions for the reaction of II with IV (process (b)) correspond to those stated for process (a) in respect of the solvents used, the bases as acid acceptors and the temperatures. In order to keep the formation of by-products, in particular ethers formed from 2 moles of II, at a very low level, the compound IV is advantageously used is not less than a two-fold molar excess, or a compound in which X and Y differ is employed, so that the different reactivities can be utilized, as is the case with, for example, bromine compared with chlorine.

The resulting intermediates of the formula IX

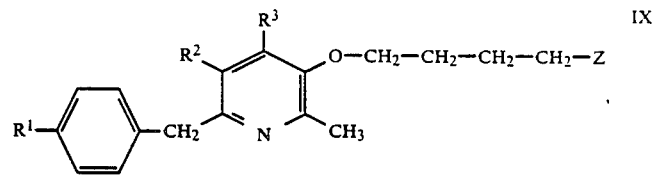

IX can be isolated and then reacted with an amine $NH_2R^4$ or can be reacted with the amine directly in the reaction mixture obtained from the first process step.

As in the above case, this reaction too is advantageously carried out in a solvent and in the presence of a base. The base used may be an excess of the amine $NH_2R^4$, which may simultaneously serve as a solvent. The reaction is carried out at elevated temperatures, in general at from 60° to 120° C., under atmospheric pressure or, if necessary, in a closed vessel under superatmospheric pressure, particularly when a readily volatile amine is used.

The alkylation of the amine according to a process (c) is advantageously carried out in a lower alcohol, preferably methanol or ethanol, in the presence of a base as an acid acceptor, preferably sodium carbonate, at room temperature or elevated temperatures up to the reflux temperature.

A compound of the formula I, where $R^4$ is isopropyl, may also be prepared by reductive alkylation of the amine. This reaction is preferably carried out as a catalytic hydrogenation reaction in the presence of platinum.

The starting materials required for the preparation processes are obtainable by conventional processes (cf. for example German Laid-Open Application DOS No. 2,711,655).

The compounds of the formula VI can be prepared by heating a compound IX, dissolved in a lower alcohol, such as ethanol, with excess ammonia in a closed system. They can also be obtained by heating a compound of the formula IX dissolved in a polar solvent, in particular dimethylformamide, with potassium phthalimide to form the corresponding phthalimide derivative, and reacting the latter with hydroxylamine, preferably in a lower alcohol, such as methanol, and in the presence of an alcoholate, such as sodium methylate.

Depending on the process conditions and starting compounds, the novel compounds are obtained in free form or in the form of their acid addition salts, which are likewise embraced by the invention. The acid addition salts may be basic, neutral or mixed salts, if desired in the form of hydrates. The acid addition salts obtained in the preparation process can be converted to the free base in a conventional manner using a basic agent, such as an alkali or an ion exchanger. On the other hand, the free bases obtained can be converted to the salts directly with organic or inorganic acids.

If necessary, the acid addition salts, such as the picrates or perchlorates, may also be used for purifying the compounds obtained, this being done by converting the free bases into these salts, separating off the latter and liberating the bases again from the salts.

Depending on the choice of the starting compounds and procedures, some of the novel compounds can be obtained in the form of optical antipodes or racemates. The racemates obtained can be resolved into the optical antipodes by a conventional method, for example by reaction with an optically acid which forms salts with the racemic compound, and separation of the mixture into the diastereomers, or with the aid of microorganisms or by recrystallization from an optically active solvent. Particularly useful optically active acids are, for example, the D- and L-forms of tartaric acid, malic acid, mandelic acid and camphorsulfonic acid.

The novel compounds have a powerful antiarrhythmic action and are useful for the therapy of cardiac arrhythmias. The pharmacological investigations to determine the antiarryhythmic action were carried out using the antiarrhythmic barucainid as a comparison.

The test animals used were male Sprague-Dawley rats weighing 180–300 g. Anesthesia was effected with 100 mg/kg of thiobutabarbital, administered intraperitoneally. To induce arrhythmias, aconitine was infused at a dosage rate of 5 μg per kg per min. The test substances were administered intravenously, directly before the beginning of the aconitine infusion. The parameter measured is the amount of aconitine which leads to the first signs of arrhythmias (disappearance of P, ventricular extrasystoles and tachycardia) in the ECG of the animals. In the case of untreated animals, the arrhythmogenic aconitine dose was 16.5±0.34 μg/kg (n=120). The dose which causes a 50% increase was determined from the linear relationship between log dose (mg/kg) of the test substances and the relative increase in the arrhythmogenic aconitine dose ($\Delta\%$).

The maximum effect achieved ($\Delta\%$) is evaluated as a further criterion of the antiarrhythmic efficacy.

The dose of test substance which causes toxic changes in the ECG (ST depression, disappearance of P, extrasystoles) was also determined. The quotient of the ECG-toxic dose and the antiarrhythmic ED 50 was evaluated as a measure of the therapeutic index of the novel compounds.

The Table shows the antiarrhytmic effect (ED 50), the maximum effect achieved ($\Delta\%$) and the therapeutic index of the novel compounds.

Comparison of the ED 50 values shows that the substances of Examples 1, 2 and 3 have an action which is from 2.8 to 10.3 times more powerful than that of barucainid. Furthermore, the substances of Examples 2, 3 and 4 are superior to barucainid in respect of the maximum effect achieved. The therapeutic index of all substances is substantially greater than that of barucainid.

TABLE 1

Antiarrhythmic effect and therapeutic index in the rat

| Example No. | Antiarrhythmic effect[1] | | ECG-toxic[2] dose (mg/kg) | Therapeutic index[3] |
|---|---|---|---|---|
| | ED 50 (mg/kg) | Maximum effect ($\Delta\%$) | | |
| Barucainid | 1.95 | 105 | 10.0 | 5.13 |
| 1 | 0.190 | 111 | 2.15 | 11.3 |
| 2 | 0.468 | 239 | >4.64 | >9.9 |
| 3 | 0.695 | 276 | 10 | 14.4 |
| 4 | 2.69 | 263 | 46.4 | 17.3 |

[1]Antiarrhythmic effect on the aconitine-induced arrhythmia (increase in the duration of aconitine infusion until the occurrence of arrhythmias)
[2]Toxic effect in the ECG (occurrence of extrasystoles)
[3]Therapeutic index (toxic dose: ED 50)

The therapeutic agents or formulations are prepared in a conventional manner by compounding an appropriate dose with the conventional carriers or diluents and the conventional pharmaceutical auxiliaries, in accordance with the desired route of administration.

The preferred formulations are those suitable for oral administration. Examples of these are tablets, film tablets, capsules, pills, powders, solutions or suspensions or forms which exert a depot effect.

Of course, formulations for parenteral administration, eg. injectable solutions or additives for infusion solutions, are also suitable. Suppositories are a further example of suitable formulations.

Appropriate tablets can be obtained, for example, by mixing the active compound with conventional auxiliaries, for example inert diluents, such as dextrose, sugar, sorbitol, mannitol, polyvinylpyrrolidone, calcium carbonate, calcium phosphate or lactose, disintegrating agents, such as corn starch, alginic acid or polyvinylpyrrolidone, binders, such as starch or gelatine, lubricants, such as magnesium stearate or talc and/or agents for achieving a depot effect, eg. carboxypolymethylene, carboxymethylcellulose, cellulose acetate phthalate or polyvinyl acetate. The tablets may furthermore consist of a plurality of layers.

Correspondingly, coated tablets can be prepared by coating cores, prepared similarly to the tablets, with agents conventionally used in tablet coatings, for example collidone or shellac, gum arabic, talc, titanium dioxide or sugar. The coating can also consist of a plurality of layers, and the auxiliaries mentioned above in connection with tablets may be used therein.

Solutions or suspensions containing the novel active compounds may additionally contain flavor improvers, such as saccharin, cyclamate or sugar, and, for example, flavor materials, such as vanillin or orange extract. They may also contain suspending agents, such as sodium carboxymethylcellulose, or preservatives, such as parahydroxybenzoates. Capsules containing the active compounds may be prepared, for example, by mixing the active compound with an inert carrier, such as lactose or sorbitol, and encapsulating the mixture in gelatine capsules.

Suitable suppositories can be prepared, for example, by mixing with carriers intended for this purpose, eg. neutral fats or polyethylene glycols or their derivatives.

A single dose of a novel substance for humans is from 5 to 100 mg, preferably from 10 to 80 mg.

The examples which follow illustrate the invention, without restricting it.

EXAMPLE 1

2-Methyl-3-(4-isopropylaminobutoxy)-4-(1'-morpholinomethyl-5-hydroxymethyl-6-benzylpyridine trihydrochloride

A. Preparation of the starting material (a) 203.6 g (1 mole) of pyridoxal hydrochloride (Merck, 500764) were dissolved in 1.2 l of methanol, and the solution was left to stand for 18 hours at room temperature and then refluxed, 200 ml being distilled off in the course of 3 hours. Thin layer chromatography showed that the starting material was then completely converted to the monomethyl acetal. The mixture was evaporated down to 600 ml in a rotary evaporator, the warm solution was filtered, and 300 ml of methyl tert-butyl ether were added. The mixture was left to stand for 12 hours and then filtered, and the product was washed with a 50:50 methanol/methyl tert-butyl ether mixture and dried to give 145 g of fine white needles of melting point 164° C.

(b) 120 g (0.55 mole) of the crystals were introduced into 250 ml of morpholine under nitrogen. The temperature increased to 43° C., accompanied by the formation of a yellow suspension, to which 90 g (0.85 mole) of benzaldehyde were added dropwise in the course of 10 minutes. During the addition, the temperature increased to 83° C. The mixture was heated to an internal temperature of 125° C. in the course of 2.5 hours, and low boilers were distilled off during this procedure. The mixture was then evaporated down under 20 mbar and at a bath temperature of from 50° to 100° C. 300 ml of methylene chloride were slowly added dropwise to the mechanically stirred and refluxed mixture, at 70° C. The mixture was cooled to 20° C., and 90 g (1.6 moles) of KOH in 600 ml of water were added to the dark brown solution. Stirring was continued for 5 minutes, the phases were separated in a separating funnel, and the aqueous phase was washed with 150 ml of methylene chloride, and the methylene chloride solutions were extracted twice with 75 ml of water. 300 ml of methylene chloride were added to the aqueous solutions, and the pH was brought to 8–8.2 by adding 280 ml of 10% strength HCl to the stirred mixture. The methylene chloride phase was separated off, and the aqueous phase was extracted with twice 120 ml of methylene chloride. The organic phase was dried over sodium sulfate and the solvent was stripped off to give 224 g of a viscous brown oil.

This oil was dissolved in 600 ml of methanol in an autoclave, and hydrogenated using 10 g of a catalyst (Degussa type E 10N, 10% of palladium on carbon) at 40° C. and under a hydrogen pressure of 10 bar. The hydrogenated product was stirred with 24 g of NaOH in 160 ml of water, while cooling with ice at 10° C. The mixture was filtered under suction, the residue was washed with water, and the filtrate was evaporated down to 800 ml and brought to pH 8 with hydrochloric acid. 41 g of 2-methyl-3-hydroxy-4-(1-morpholinomethyl)-5-hydroxymethyl-6-benzylpyridine of melting point 163° C. (methanol) crystallized at 10° C.

(c) 32.8 g of the product obtained in this manner were dissolved in 500 ml of acetone, and the solution was refluxed for 10 hours with 108 g of 1,4-dibromobutane and 138 g of potassium carbonate. The solvent was distilled off under reduced pressure and, in the final stage, the excess 1,4-dibromobutane was distilled off under reduced pressure from an oil pump.

B. Preparation of the end product

The product obtained as described in A. (c), in 50 ml of isopropylamine, was reacted at room temperature for 20 hours. 2N NaOH was added to the evaporation residue, and the mixture was extracted with ethyl acetate. The combined extracts were dried over magnesium sulfate, and the solution was filtered and evaporated down to give 30 g of the free base of the end product. An ether solution of hydrochloric acid was added to this product in 80 ml of ethanol. The resulting crude crystals were recrystallized from ethanol to give 26 g of 2-methyl-3-(4-isopropylaminobutoxy)-4-(1'-morpholinomethyl)-5-hydroxymethyl-6-benzylpyridine trihydrochloride of melting point 204°–205° C.

EXAMPLE 2

1-Hydroxy-4-benzyl-6-methyl-7-(4-isopropylaminobutoxy)-1,3-dihydrofuro[3,4-C]pyridine dihydrochloride

A. Preparation of the starting material 30.0 g (0.115 mole) of 6-benzylpyridoxine were dissolved in 1.5 l of water and 3.5 ml of 4N sulfuric acid. Nitrogen was passed through the solution, and 170 g ((1.95 moles) of manganese dioxide were introduced a little at a time in the course of 30 minutes. Stirring was continued for 3.5 hours at room temperature, the inorganic material was filtered off and the residue was washed with water. The filtrate was evaporated down in a rotary evaporator, the residue was taken up in 500 ml of methanol and the solution was again filtered under suction. The yellow filtrate was evaporated to dryness, and the residue was dissolved in 2 l of methanol. After standing for 2 days at room temperature, the solution was evaporated down to give 21 g of residue, which was brought to pH 8.5 with sodium bicarbonate. The solid material was filtered off under suction and recrystallized from methanol. 14.0 g of 1-methoxy-4-benzyl-6-methyl-7-hydroxy-1,3-dihydrofuro[3,4-C]pyridine were obtained as yellow needles of melting point 177°–178° C. (decomposition).

The product obtained in this manner was converted to the corresponding 4-bromobutoxy compound.

To do this, 10 g of the product were dissolved in 500 ml of acetone, 43 g of 1,4-dibromobutane and 110 g of $K_2CO_3$ were added, the mixture was refluxed for 5 hours and then filtered under suction, and the residue was washed with acetone and evaporated down under reduced pressure, in the final stage at 60° C. 16 g of a brownish oil were obtained.

By dissolving the product in 50 ml of isopropylamine at 25° C., leaving the solution to stand for 48 hours and then distilling off the excess amine, 1-methoxy-4-benzyl-6-methyl-7-(4-isopropylaminobutoxy)-1,3-dihydrofuro[3,4-C]pyridine was obtained in the form of a brown resin.

B. Preparation of the end product

Without further purification, the product obtained as described in A was kept in 100 ml of HCl for 16 hours at room temperature, 2 g of active carbon were added and the mixture was then stirred for 1 hour and filtered. The paper filter was washed with water, and the solution was evaporated down to 50 ml under reduced pressure at 50° C. The residue was saturated with ethylene glycol dimethyl ether and left to stand for 20 hours at 20° C., after which the solution was filtered. Washing with an H$_2$O/ethylene glycol dimethyl ether mixture and finally with the pure solvent gave 9 g of crystalline 1-hydroxy-4-benzyl-6-methyl-7-(4-isopropylaminobutoxy)-1,3-dihydrofuro[3,4-C]pyridine dihydrochloride of melting point 194°–197° C.

EXAMPLE 3

3-Hydroxy-4-benzyl-6-methyl-7-(4-isopropylaminobutoxy)-1,3-dihydrofuro[3,4-C]pyridine

A. Preparation of the starting material (a) 6-Benzylpyridoxine was reacted with sulfuric acid and acetone, while cooling in an ice bath and stirring thoroughly, by a procedure similar to that described by H. Cohen and E. G. Hughes, J. Chem. Soc. (1952), 4384, to give the acetonide. This process gave an isomer mixture which predominantly contained the desired 6-membered cyclic $\alpha^4$, $\alpha^5$-acetal with respect to the phenolic hydroxyl group. The well cooled and thoroughly stirred mixture was neutralized by pouring it into excess aqueous sodium hydroxide solution which was covered with a layer of ethyl acetate. Extraction of the aqueous phase with several portions of ethyl acetate, washing with 2N NaOH and H$_2$O, drying over K$_2$CO$_3$, filtering and evaporating down at 40° C. in a rotary evaporator gave a pale brown oil. The desired pure acetonide of melting point 120°–121° C. crystallized from petroleum ether, in the form of colorless needles.

(b) 13 g of this product wwere dissolved in 1500 ml of acetone, and the solution was cooled to 5° C. 200 g of manganese dioxide were added and after 20 hours the acetone phase was filtered and the filtrate was evaporated down to give $\alpha^4$,3-O-isopropylidene-6-benzyl-pyridoxal in a yield of 95%.

(c) The product obtained in this manner was dissolved in 60 ml of 2N hydrochloric acid, without further purification. Beige crystals were formed very rapidly. The solid material was brought into solution by stirring at 50° C., and the acetonide was completely hydrolyzed after 3 hours. The solution was evaporated down at 50° C. in a rotary evaporator, the residue was taken up in 1500 ml of methanol, and the solution was refluxed for 17 hours and then evaporated down again. 3-Methoxy-4-benzyl-6-methyl-7-hydroxy-1,3-dihydrofuro[3,4-C]pyridine was obtained.

(d) The product obtained in this manner was dissolved in 1000 ml of acetone, and the stirred solution was refluxed with 100 g of potassium carbonate and 90 g of 1,4-dibromobutane for 15 hours. The mixture was filtered under suction, the residue was washed thoroughly with acetone, the solution was evaporated down and excess 1,4-dibromobutane was distilled off at 50° C. under greatly reduced pressure to give 17 g of a pale brown, viscous oil.

(e) The product obtained as described in (d) was dissolved in 100 ml of isopropylamine, without further purification, and the solution was kept at room temperature for 6 hours. It was then evaporated down again, the residue was dissolved in methanol and the solvent and residual isopropylamine were removed under reduced pressure. The evaporation residue consisting of 29 g of a brown oil was partitioned in 10 ml of 5N NaOH and 50 ml of methyl tertbutyl ether. The alkaline phase was washed with methyl tert-butyl ether, and the organic phase was dried over potassium carbonate and evaporated down to give 17 g of a pale brown resin.

B. Production of the end product

The product obtained as described in A. (e), in 100 ml of 2N HCl and 200 ml of H$_2$O, was stirred for 17 hours at room temperature and then evaporated down at 50° C. in a rotary evaporator. Ethylene glycol dimethyl ether was added to the residue, and the mixture was left to stand for 2 days at 3° C. The crystals were filtered off under suction, washed with water/glycol ether and dried. 7 g of 3-hydroxy-4-benzyl-6-methyl-7-(4-isopropylaminobutoxy)-1,3-dihydrofuro[3,4-C]pyridine dihydrochloride of melting point 188° C. were obtained.

EXAMPLE 4

(p-Hydroxybenzyl)-6-methyl-7-(4-isopropylaminobutoxy)-1,3-dihydrofuro[3,4-C]pyridine

A. Preparation of the starting material (a) 24 g of 2-methyl-4,5-epoxydimethylpyridin-3-ol were added to 63.6 g (0.73 mole) of morpholine at 23° C., while stirring, and, after 10 minutes, 35.7 g of p-tert-butoxybenzaldehyde were rapidly added dropwise. The stirred mixture was heated to 120° C. and allowed to cool to an internal temperature of 100° C. after 3 hours, and unconverted morpholine was distilled under 36 bar. The residue was dissolved in 80 ml of methylene chloride at 60° C., the solution was cooled to 10° C., and a solution of 17 g of KOH and 100 ml of water was added dropwise. The aqueous phase was separated off and extracted with twice 50 ml of methylene chloride. The alkaline solution was stirred with 150 ml of methylene chloride and cooled in an ice bath. The pH was brought to 9 by adding 5N HCl. The aqueous phase was washed with methylene chloride, and the combined extracts were dried over sodium sulfate and evaporated down. 74 g of Crude 6-[($\alpha$-morpholino)-4-tert-butoxybenzyl]-1,3-dihydrofuro[3,4-C]pyridine were obtained.

(b) 25 g of this product were dissolved in 0.5 l of glacial acetic acid and hydrogenated using 50 g of 10% strength palladium/carbon catalyst at 60° C. and under 100 bar. The catalyst was filtered off under suction and washed with 1 l of glacial acetic acid. The filtrate was evaporated down to give 34 g of a pale brown oil, which was dissolved in 100 ml of ethyl acetate, and the solution was added to a cooled solution of 120 g of potassium carbonate in 400 ml of water. The resulting suspension was thoroughly extracted with ethyl acetate, and the combined extracts were dried over sodium sulfate and filtered. After the solution had been evaporated down to 400 ml, crystallization began, 8.2 g of 6-(4-butoxybenzyl)-1,3-dihydrofuro[3,4-C]pyridine of melting point 213°-215° C. being obtained overnight at room temperature.

(c) 4.0 g (13.2 millimoles) of this product were stirred with 20 g of potassium carbonate in 250 ml of acetone for 15 minutes. 10 ml (84 millimoles) of 1,4-dibromobutane were added, and the thoroughly stirred mixture was refluxed. After 4 hours, the mixture was cooled and filtered under suction, and the salt which had separated out was washed with acetone. The filtrate was evaporated down and the excess dibromobutane was distilled off under reduced pressure from an oil pump.

B. Preparation of the end product

A pale brown oil (6 g) obtained as described in A. (c) was dissolved in 30 ml of isopropylamine. After 5 hours, the solution was evaporated down in a rotary evaporator, and the residue of 10.5 g was stirred in 100 ml of 2N HCl for 2 days at room temperature. Active carbon was added, the solution was filtered under suction and the residue was washed with water. Evaporation gave 7.9 g of crude product, which was brought to pH 8 with sodium bicarbonate solution. The solution was decanted from a small amount of resin, and a colorless solid was precipitated with further sodium bicarbonate solution. 4.0 g (81%) of 4-(p-hydroxybenzyl)-6-methyl-7-(4-isopropylaminobutoxy)-1,3-dihydrofuro[3,4-C]pyridine of melting point 59°-61° C. were obtained.

The following compounds may be prepared by a similar method:

2-methyl-3-(4-propylaminobutoxy)-4-(1'-morpholinomethyl)-5-hydroxymethyl-6-benzylpyridine, 2-methyl-3-(4-propylaminobutoxy)-4-(1'-pyrrolidinomethyl)-5-hydroxymethyl-6-benzylpyridine, 2-methyl-3-(4-propylaminobutoxy)-4-(1'-pyridinomethyl)-5-hydroxymethyl-6-benzylpyridine, 2-methyl-3-(4-propylaminobutoxy)-4-(1'-dimethylaminomethyl)-5-hydroxymethyl-6-benzylpyridine, 2-methyl-3-(4-propylaminobutoxy)-4-(1'-diethylaminomethyl)-5-hydroxymethyl-6-benzylpyridine, 2-methyl-3-(4-propylaminobutoxy)-4-(1'-morpholinomethyl)-5-hydroxymethyl-6-p-hydroxybenzylpyridine, 2-methyl-3-(4-propylaminobutoxy)-4-(1'-pyrrolidinomethyl)-5-hydroxymethyl-6-p-hydroxybenzylpyridine, 2-methyl-3-(4-propylaminobutoxy)-4-(1'-pyridinomethyl)-5-hydroxymethyl-6-p-hydroxybenzylpyridine, 2-methyl-3-(4-propylaminobutoxy)-4-(1'-dimethylaminomethyl)-5-hydroxymethyl-6-p-hydroxybenzylpyridine, 2-methyl-3-(4-propylaminobutoxy)-4-(1'-diethylaminomethyl)-5-hydroxymethyl-6-p-hydroxybenzylpyridine, 2-methyl-3-(4-butylaminobutoxy)-4-(1'-morpholinomethyl)-5-hydroxymethyl-6-benzylpyridine, 2-methyl-3-(4-butylaminobutoxy)-4-(1'-pyrrolidinomethyl)-5-hydroxymethyl-6-benzylpyridine, 2-methyl-3-(4-butylaminobutoxy)-4-(1'-pyridinomethyl)-5-hydroxymethyl-6-benzylpyridine, 2-methyl-3-(4-butylaminobutoxy)-4-(1'-dimethylaminomethyl)-5-hydroxymethyl-6-benzylpyridine, 2-methyl-3-(4-butylaminobutoxy)-4-(1'-diethylaminomethyl)-5-hydroxymethyl-6-benzylpyridine, 2-methyl-3-(4-butylaminobutoxy)-4-(1'-morpholinomethyl)-5-hydroxymethyl-6-p-hydroxybenzylpyridine, 2-methyl-3-(4-butylaminobutoxy)-4-(1'-pyrrolidinomethyl)-5-hydroxymethyl-6-p-hydroxybenzylpyridine, 2-methyl-3-(4-butylaminobutoxy)-4-(1'-pyridinomethyl)-5-hydroxymethyl-6-p-hydroxybenzylpyridine, 2-methyl-3-(4-butylaminobutoxy)-4-(1'-dimethylaminomethyl)-5-hydroxymethyl-6-p-hydroxybenzylpyridine, 2-methyl-3-(4-butylaminobutoxy)-4-(1'-diethylaminomethyl)-5-hydroxymethyl-6-p-hydroxybenzylpyridine, 1-hydroxy-4-benzyl-6-methyl-7-(4-n-propylaminobutoxy)-1,3-dihydrofuro[3,4-C]pyridine dihydrochloride, 1-hydroxy-4-benzyl-6-methyl-7-(4-n-butylaminobutoxy)-1,3-dihydrofuro[3,4-C]pyridine dihydrochloride 1-hydroxy-4-benzyl-6-methyl-7-(4-isobutylaminobutoxy)-1,3-dihydrofuro[3,4-C]pyridine dihydrochloride, 1-methoxy-4-benzyl-6-methyl-7-(4-n-propylaminobutoxy)-1,3-dihydrofuro[3,4-C]pyridine dihydrochloride, 1-methoxy-4-benzyl-6-methyl-7-(4-n-butylaminobutoxy)-1,3-dihydrofuro[3,4-C]pyridine dihydrochloride, 1-methoxy-4-benzyl-6-methyl-7-(4-isobutylaminobutoxy)-1,3-dihydrofuro[3,4-C]pyridine dihydrochloride, 1-methoxy-4-benzyl-6-methyl-7-(4-isopropylaminobutoxy)-1,3-dihydrofuran[3,4-C]pyridine dihydrochloride, 3-methoxy-4-benzyl-6-methyl-7-(4-isopropylaminobutoxy)-1,3-dihydrofuran[3,4-C]pyridine 3-methoxy-4-benzyl-6-methyl-7-(4-n-propylaminobutoxy)-1,3-dihydrofuro[3,4-C]pyridine 3-methoxy-4-benzyl-6-methyl-7-(4-n-butylaminobutoxy)-1,3-dihydrofuro[3,4-C]pyridine 3-methoxy-4-benzyl-6-methyl-7-(4-isobutylaminobutoxy)-1,3-dihydrofuro[3,4-C]pyridine 3-hydroxy-4-benzyl-6-methyl-7-(4-isopropylaminobutoxy)-1,3-dihydrofuro[3,4-C]pyridine 3-hydroxy-4-benzyl-6-methyl-7-(4-n-propylaminobutoxy)-1,3-dihydrofuro[3,4-C]pyridine 3-hydroxy-4-benzyl-5-methyl-7-(4-n-butylaminobutoxy)-1,3-dihydrofuro[3,4-C]pyridine, 3-hydroxy-4-benzyl-6-methyl-7-(4-isobutylaminobutoxy)-1,3-dihydrofuro[3,4-C]pyridine, 4-p-hydroxybenzyl-6-methyl-7-(4-isopropylaminobutoxy)-1,3-dihydrofuro[3,4-C]pyridine, 4-p-hydroxybenzyl-6-methyl-7-(4-n-butylaminobutoxy)-1,3-dihydrofuro[3,4-C]pyridine, 4-p-hydroxybenzyl-6-methyl-7-(4-isobutylaminobutoxy)-1,3-dihydrofuro[3,4-C]pyridine.

We claim:

1. 2-Methyl-3-(4-isopropylaminobutoxy)-4-(1'-morpholinomethyl)-5-hydroxymethyl-6-benzylpyridine.

2. 1-Hydroxy-4-benzyl-6-methyl-7-(4-isopropylaminobutoxy)-1,3-dihydrofuro[3,4-C]pyridine dihydrochloride.

3. 3-Hydroxy-4-benzyl-6-methyl-7-(4-isopropylaminobutoxy)-1,3-dihydrofuro[3,4-C]pyridine.

* * * * *